United States Patent [19]

McCormick

[11] Patent Number: 4,576,796
[45] Date of Patent: Mar. 18, 1986

[54] CENTRIFUGAL TISSUE PROCESSOR

[75] Inventor: James B. McCormick, Chicago, Ill.

[73] Assignee: Pelam, Inc., Chicago, Ill.

[21] Appl. No.: 572,168

[22] Filed: Jan. 18, 1984

[51] Int. Cl.[4] ................ G01N 1/06; G01N 1/28; G01N 33/48
[52] U.S. Cl. .................... 422/99; 118/52; 422/72; 427/4; 435/312
[58] Field of Search ............ 422/63, 64, 72, 99, 422/100, 102; 427/2, 4, 24; 118/52; 494/20; 435/312

[56] References Cited

U.S. PATENT DOCUMENTS

| | | | |
|---|---|---|---|
| 3,870,789 | 3/1975 | Mikat | 422/72 |
| 3,901,658 | 8/1975 | Burtis et al. | 422/72 |
| 3,953,172 | 4/1976 | Shapiro et al. | 422/72 |
| 4,141,312 | 2/1979 | Louder et al. | 422/99 |
| 4,192,250 | 3/1980 | Duijn | 422/72 |
| 4,225,558 | 9/1980 | Peterson et al. | 422/72 |
| 4,256,696 | 3/1981 | Soodak | 422/64 |
| 4,320,157 | 3/1982 | Hagens | 427/4 |
| 4,360,360 | 11/1982 | Chiknas | 422/64 |
| 4,373,812 | 2/1983 | Stein et al. | 422/72 |
| 4,470,954 | 9/1984 | Chiknas | 422/72 |
| 4,483,270 | 11/1984 | Toya et al. | 118/702 |

Primary Examiner—Arnold Turk
Attorney, Agent, or Firm—Fitch, Even, Tabin & Flannery

[57] ABSTRACT

Tissue samples are prepared for embedding and then embedded within wells of an intermittently rotatable rotor. After each successive liquid is supplied to the sample wells, the rotor is spun in order to slough off liquid from the samples. The sloughed liquid is collected by an outer shroud. The shroud is preferably made fluid tight so that the interior region of the shroud can be communicated to vacuum to force embedding material into the interstices of the tissue samples.

14 Claims, 8 Drawing Figures

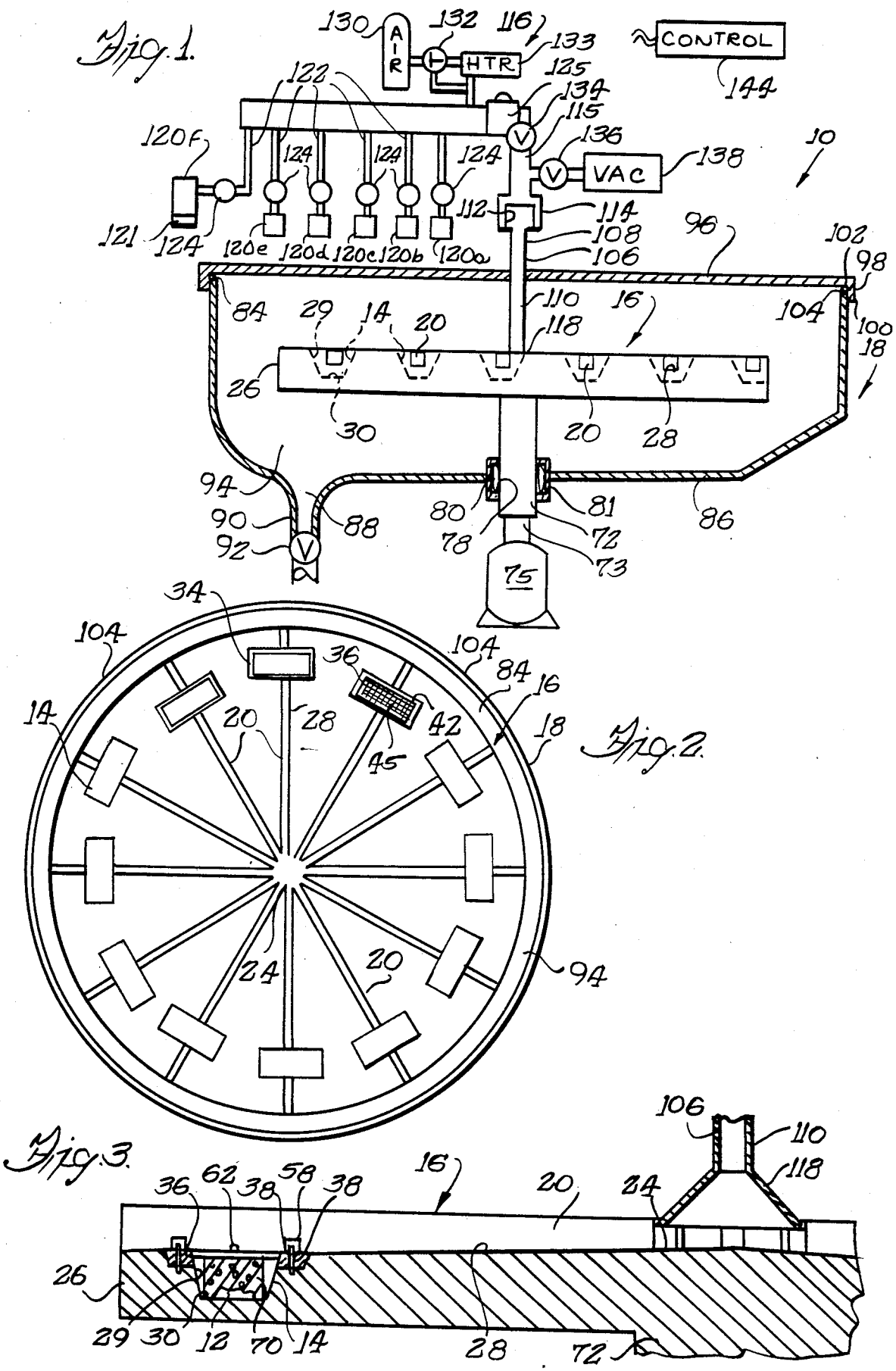

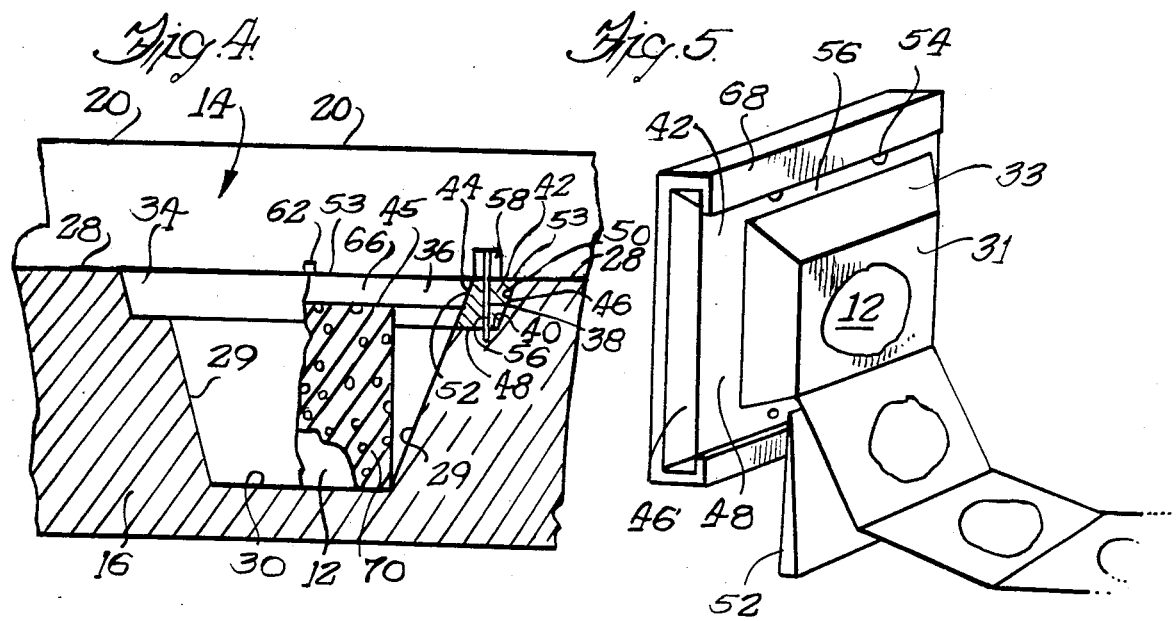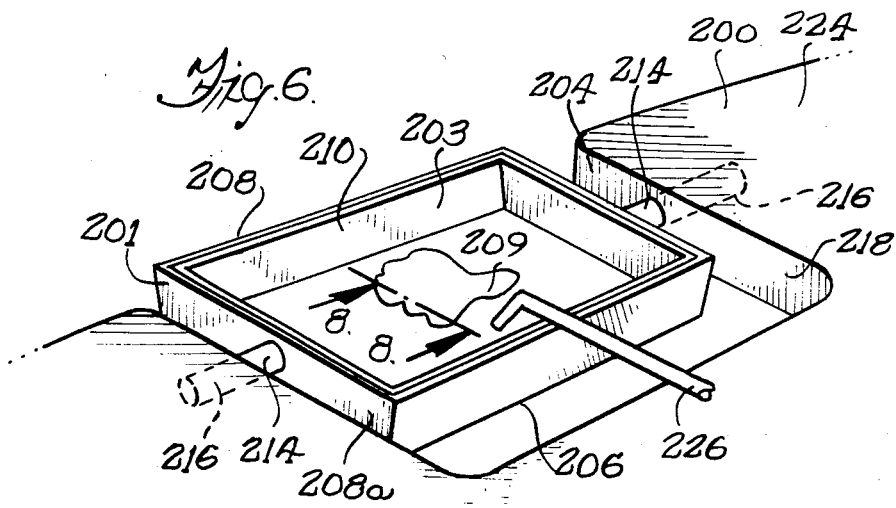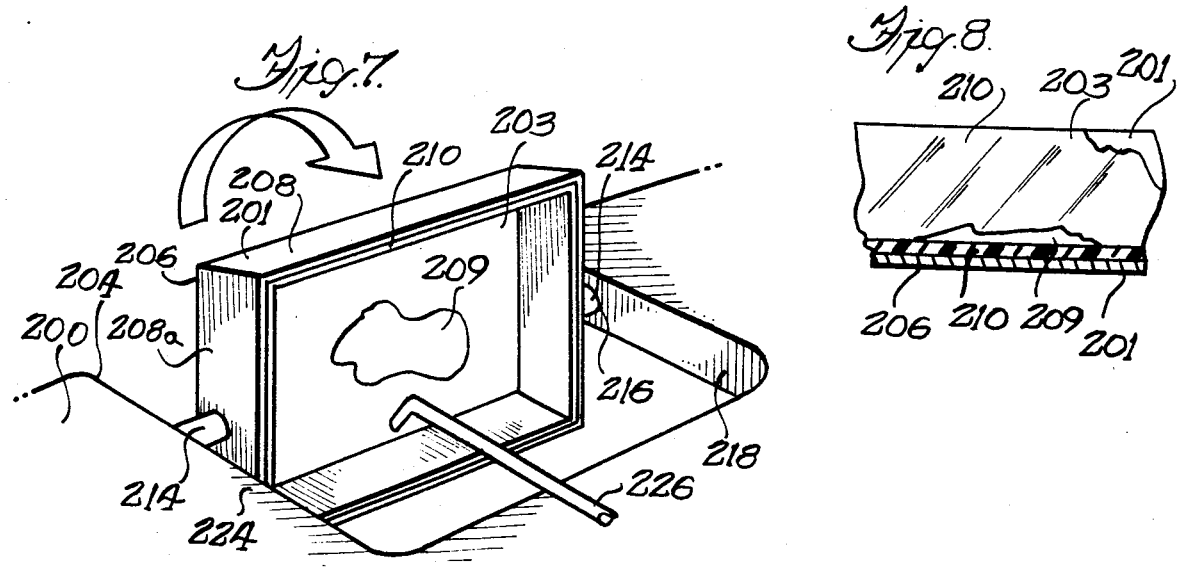

CENTRIFUGAL TISSUE PROCESSOR

The present invention relates to apparatus for tissue sample preparation and more particularly to apparatus for processing tissue samples and embedding them preparatory to slicing for subsequent microscopic examination.

BACKGROUND OF THE INVENTION

In the course of current medical practice, an increasing number of tissue samples are presented for histological examination. The tissue samples are preserved by subjeciing them to various solutions including fixative solutions, dehydrating solutions and clearing solutions. Subsequently, the tissue sample is embedded in material, typically paraffin or another suitable embedding wax, and then sliced very thinly with a microtome for microscopic examination.

A substantial portion of a histology technician's time is frequently occupied with preparation of tissues, generally routine procedures which utilize time that might be better spent on other work. Although the processing and embedding protocols are routine, these protocols must be carefully adhered to in order to obtain an embedded tissue sample from which precise tissue sections may be prepared. Generally protocols require that the tissue sample be soaked in each processing liquid for a time sufficient for the processing liquid to fully penetrate into all portions of the tissue. Each processing liquid should be substantially completely removed before the next processing liquid is introduced.

It is a general object of the present invention to provide apparatus by which most of the steps of preparing tissue samples for examination can be effected automatically without the constant attention of the technician. It is a further object of the invention to provide apparatus which more effectively provides for complete exchange of processing and embedding fluids.

SUMMARY OF THE INVENTION

Apparatus is provided for automatically supplying processing liquids to tissue samples and subsequently removing the processing liquids. Tissue wells are provided along the periphery of a rotor and means are provided for supplying processing liquids to the tissue wells. After the tissues have been processed in each liquid, the rotor is spun, so that it sloughs off the liquid in the wells. A shroud surrounding the rotor collects the sloughed off liquids some of which may then be recovered and recycled.

BRIEF DESCRIPTION OF THE DRAWINGS

FIG. 1 is an illustration of tissue sample processing apparatus embodying various features of the invention, a rotor in which is formed sample wells being shown in elevation, a shroud surrounding the rotor being shown in cross section, and auxiliary apparatus shown in block diagram;

FIG. 2 is a plan view of the rotor and shroud of FIG. 1 with the cover of the shroud removed;

FIG. 3 is a cross-sectional view taken along line 3—3 of FIG. 2, also showing covers for the sample wells;

FIG. 4 is an enlarged cross-sectional view of one of the sample wells;

FIG. 5 is a perspective view of a tissue embedded in a block of embedding materal that is attached to one of the well covers and held in a microtome chuck in position for microtome slicing;

FIG. 6 is a perspective view of a portion of a rotor of an alternate embodiment of a centrifugal tissue processor of the present invention;

FIG. 7 is a view similar to FIG. 6 but showing the rotor in motion; and

FIG. 8 is a cross-sectional view taken along line 8—8 of FIG. 6.

DETAILED DESCRIPTION OF THE PREFERRED EMBODIMENT

In accordance with the present invention, apparatus, indicated generally as 10, is provided which uses centrifugal force to effect automatic and rapid exchange of tissue processing liquids. Tissue samples 12 (FIG. 3) are positioned in wells 14 disposed around the periphery of an intermittently operated rotor 16. Successive processing liquids are provided to the wells 14, and after the tissue samples 12 in the wells have been exposed to each processing liquid for a sufficient period of time, the rotor 16 is spun at a speed sufficient to substantially completely slough off all of the processing liquid. A shroud 18 surrounding the rotor 16 collects the sloughed processing liquid.

The rotor 16, generally in the shape of a flat disc, has the sample wells 14 and several channels 20 formed into its upper face. The channels 20 extend radially outward from a circular central well 24 to which processing liquids are supplied for conducting the liquid to the peripheral sample wells 14 and continue from the wells outward to the edge 26 of the rotor 16 for conducting overflow liquid that has been supplied to the wells and later spent processing liquids that are spun from the wells. The channels 20 preferably have flat bottom surfaces 28 that slope downward slightly, e.g., between about 2° and about 5°, from the shallow central well 24.

The sample wells 14 serve as molds in the final embedding stage of the process and have a configuration adapted for formation of a block of embedding material suitable for microtome slicing. The wells 14 each have rectangular horizontal cross sections and have sidewalls 29 that slope inward so that the well narrows towards its bottom surface 30. The bottom surface 30 of each well is flat because it is the surface 31 (FIG. 5) of the block 33 of embedding material that forms complementary to this bottom surface that is presented to a microtome 52 for slicing. The upper end of each well is a widened peripheral region 34 that receives a well cover 36. Pins 38 (FIG. 4) extend upward from a lower surface 40 of peripheral region for locating and holding the well cover 36.

Each well cover 36 includes a disposable rectangular frame 42 providing an interior opening 44 across which is spread a porous mesh 45 that accesses processing liquid to the well 14 while retaining the tissue therein. The exterior frame surfaces 46 and bottom frame surfaces 48 are matched to the interior walls 50 and bottom surface 40 of the peripheral region 34. The interior frame surfaces 52 are generally continuous of the well sidewalls 29 and the upper frame surface 53 is flat and generally continuous of the flat bottom 28 of the radial channel 20. Holes 54 through the trans-radial frame sides 56 (FIG. 5) fit over the upwardly extending pins 38, and each receive a fitting 58 at its upper end to secure the covers 36 in place over the well 14. Small upwardly extending protrusions 60 for gripping in the radial sides 62 of the cover frame 42 facilitate its removal from the wells 14.

The well covers 36 not only serve to enclose the sample-containing regions defined by the wells 14 but serve as mountings for the blocks 33 of tissue-containing embedding material. The mesh 45 that is spread across the frame opening 44 is disposed below the upper surface 53 of the cover frame 42 defining a region 66 thereabove that is to be at least partially filled with embedding material. When the embedding material solidifies, the block 33 is integral with the cover 36, and the cover frame 42 is directly insertable in a microtome chuck 68 with the block protruding outward as seen in FIG. 5.

Proper histological examination depends in many cases on precise orientation of the tissue sample 12, and it is important that the tissue sample remain orientated in the precise position that the histology technician selects. To prevent dislocation of the tissue sample 12 as liquids are flowed into the wells 14 and when the rotor is spun, pads 70 of spongy, open pore material, such as polyurethane foam, are placed in the wells 14 over the tissue samples 12 and compressed by the mesh 45 of the well covers 36 placed thereon top. The open pore structure Of the pad 70 provides for absorbed liquid to spin out when the rotor is spun.

The rotor 16 is preferably made of metal, such as stainless steel. Surfaces which are exposed to processing liquids are preferably coated with a stick-resistant polymer coating, such as polytetrafluorethylene, to prevent the processing liquids and embedding material from sticking thereto. It is particularly important that the wells 14 be coated with a material with minimal adherence to the embedding material, e.g., paraffin, so that solidified embedding material is readily released therefrom. Other times, The rotor 16 is driven by means of a shaft 72 that extends downward from its center and is either directly or indirectly attached to a shaft 73 of a driving motor 75. The rotor shaft 72 extends through a lower opening 78 in the shroud 18, an 0-ring 80 within a bushing 81 maintaining a fluid tight seal around the shaft.

The shroud 18 is generally bowl-shaped, surrounding the rotor for collecting any liquid or any other material which flows from the rotor and having an open upper end 84 providing easy access to the sample wells 14 on the upper surface of the rotor 16. The bottom 86 of the shroud 74 slopes toward an eccentric drain opening or sump 88 connected to a drain conduit 90 leading to waste, and/or a processing liquid recycling system (not shown). The sump 88 has a valve 92 which can be closed when it is desired that the interior region 94 of the shroud 18 be made fluid tight. The interior surfaces of the shroud are preferably coated with a stick-resistant polymer so as to be generally self-cleaning.

The interior region 94 of the shroud 18 is enclosed by means of a shroud cover 96, shown in FIG. 1 as a generally flat disc. The shroud cover 96 has a depending interiorly threaded lip 98 which engages exterior threads 100 at the upper end of the shroud and carries a gasket 102 that forms a peripheral seal with the upper edge 104 of the shroud 18. Fluid access to the shroud 18 is provided by a central tubular conduit 106 through the shroud cover 96, including an upwardly extending portion 108 and a downwardly extending portion 110. The upwardly extending portion 108 has a quick-release fitting 112 for attachment to a complementary fitting 114 of an inlet conduit 115 leading from a fluid supply system, indicated generally at 116. The lower end 118 of the tubular conduit is bell-shaped and extends to closely adjacent the bottom of the central well 24 (FIG. 3) for broadly and evenly distributing a stream of liquid across the bottom of the central well. The bell-shaped lower end 118 extends radially to closely adjacent the sides of the central well 24 to prevent splashing of incoming liquids.

The fluid supply system includes a plurality of reservoirs 120 connected by conduits 122 having individual valves 124 whereby successive liquids can be drawn through the inlet conduit 115 by a pump 125. Typically a fluid supply system will include a water reservoir 120a, a fixative reservoir 120b, a dehydrating liquid reservoir 120c, a clearing liquid reservoir 120d, and a liquid embedding material reservoir 120e including a heating unit 121. The inlet conduit may also be communicated to a source 130 of pressurized air by valve 132, and as a means to heat the interior region of the shroud, a heater 133 at certain times heats the incoming pressurized air. A valve 134 is provided to close off the inlet conduit 115 from all of the reservoirs 120 and air source 130 at times when it is desirable to open a valv 136 that communicates the inlet conduit 115 to a vacuum source 138.

The various valves, the motor, the air heater etc., are all controlled by a central control unit 144, which is preferably a microprocessor that is programmed to run a complete cycle of processing from initial fixation to final embedding. After the samples have been carefully positioned in each well 14, the sponge pads 70 and well covers 36 applied, the shroud 18 is covered and the cover conduit tube 106 is connected to the inlet conduit 115 of the processing liquid supply system 116. Initially, the valve 134 in the inlet conduit 115 as well as the valve from the fixative reservoir 120b are opened to introduce fixative into the wells. The fixative is introduced slowly in order that it absorbs into the spongy pads 70, and when the tissue sample wells 14 have been filled, the valve 120b from the fixative reservoir is closed. After a predetermined amount of soaking time that assures proper fixation of the tissue samples, the fixative is removed from the wells by activating the motor 76 to spin the rotor 16. All fixative solution in the rotor 16 is driven up the inclined outer sidewalls 29 of the wells 14, including the fixative absorbed in the pads 70.

To slough all liquid from the tissue sample 12 and from the pads 70, it is preferred that the rotor 16 be spun at sufficient speed to subject the liquid in the wells to sufficient acceleration. With the rotor 16 spinning, the valve 92 in the drain conduit 90 leading from the sump 88 is opened to drain sloughed-off fixative solution. The fixative solution may either be drained to apparatus that purifies the same for recycling into the fixative reservoir or drained to a waste reservoir for disposal. Optionally, the source 130 of pressurized air may be communicated by three-way valve 132 directly to the interior of the shroud 18 after spinning of the rotor 16 and drainage of the liquid to drive any remaining liquid from the wells 14 and from the shroud 16. Also optionally, additional trace liquid may be evaporated by closing the valve 115 in the inlet conduit 134 and the valve 92 in the drain 90 and opening the valve 136 that communicates the fluid-tight interior region 94 of the shroud to vacuum 138.

The process is repeated with successive valves being opened to dehydrating liquid reservoirs 120C and clearing liquid reservoirs 120d.

After the tissue samples 12 have been thus prepared, the interior region 94 of the shroud 18 is heated using pressurized air that has been directed by three-way valve 132 through the activated heater 135. After sufficient time has passed to assure that the rotor 12 is warmed to above the melting temperature of the embedding material, the valve from the embedding material reservoir 120e is opened, and liquid embedding material is pumped into the shroud 10, filling the wells 14. After the wells are filled, the valve 134 in the inlet conduit 115 and the valve 92 in the drain conduit 90 are closed off, and the shroud interior region 94 is communicated to vacuum 138 to force the molten embedding material into the interstices of the tissue samples 12. Then additional molten embedding material is pumped into the shroud 18, assuring that all the wells 14 are filled to above the porous mesh 45 of the well covers 36.

The embedding material is allowed to cool, a process which may be hastened by passing unheated air from the pressurized air source 130 through the shroud 18. Then the cover 96 is removed from the shroud 18, the fittings 58 holding down the well covers 36 are removed and the well covers with their attached blocks 33 of tissue sample-containing embedding material are lifted from the wells. The well covers 36 are directly inserted in a microtome chuck 68 that is positioned so that flat slices may be cut from the front of the block 33 of solidified embedding material.

After removal of the well covers 36, the shroud cover 96 is reapplied in order to institute a cleaning cycle during which heated air is passed through the shroud interior 94 to melt any solidified embedding material on the surfaces of the rotor 16 or shroud 18, and both polar solvents, e.g., water from reservoir 120a, and non-polar solvents are introduced into the shroud. Preferably, introduction of each cleaning solvent is stepwise, introduction of sufficient solvent to fill the wells 14 being alternated with spinning of the rotor 16. The spinning rotor splashes cleaning solvents along the interior surfaces of the shroud cleaning the same.

Illustrated in FIGS. 6 through 8 is an alternative embodiment of the invention in which the tissue specimens 209 are processed in shallow wells 203 of "swinging bucket" type trays 201. In this embodiment, the rotor 200 is a flat circular plate formed, for example, of stainless steel and having rectangular indentations 204 at its periphery wherein the trays are pivotably mounted.

Each tray 201 is rectangular having a bottom 206, upstanding sidewalls 208 and an open upper end. In use, the interior of the tray 201 is lined with a thin plastic liner 210 in which the tissue specimen 209 is processed and embedded. The trays 201 are trunion-mounted within the rectangular indentations 204 for swinging from a horizontal position (FIG. 6) with the rotor 200 at rest to a vertical position (FIG. 7) with their bottoms 206 outward when the rotor is in motion. The mounting included cylindrical pins 214 that extend from the centers of the radially directed tray sidewalls 208a and into tangentially directed cylindrical bores 216 that are formed in the radially directed edges 218 of the indentations 204. As the rotor 200 is alternately spun and stopped, the trays 201 pivot along the axes of the pins. In the rest position of the rotor 200, the weight of the bottom 206 (and material held within the tray) holds the tray upright; however, when the rotor is spun with sufficient speed, the centrifugal force on the rotor becomes much greater than gravity, and the heavier bottom end of the tray spins to the outside, tilting the tray vertically.

As a means to provide processing liquids and embedding liquids to the trays 201, feed tubes 226 attached, e.g., as by welding, to the top 224 of the rotor 200 receive liquids from a common source (not shown) at the hub of the rotor and extend into the indentations 204, emptying into the open upper ends of the trays. The overhanging feed tubes 226 also assure that the trays do not pivot the wrong way when the rotor starts up.

A liner 210 is placed in tray 201, and then a tissue specimen 209 is placed in each liner along with a thin gelatin mix. The rotor 200 is spun as the gel hardens, flattening the tissue specimens 209 against the bottoms 206 of the tray liners 210. Next, the various processing liquids are conveyed to the trays. Some liquids may be supplied continuously, e.g., an alcohol-water gradient, in which case liquid continuously overflows from the tray and is drained through a sump (not shown). Other times, when it is desired to completely change liquids, flow through the feed tubes 226 is ceased and the rotor 200 is spun and stopped before the replacing liquid is supplied through the feed tubes. Because of the shallow configuration of the trays, most of the liquid is spilled from the trays during each spin cycle. Generally, the small amount of liquid that is retained in each spinning tray 201 is insignificant; however, in those instances where one liquid must be substantially completely replaced by another, the trays may be filled and spun two or more times with the replacing liquid.

In the final step, liquid embedding material is supplied to the trays 201, and preferably the interior of the processor is placed under vacuum to draw the embedding material into the interstices of the tissue specimens. After the embedding material has solidified, the liners 210 are removed from the trays, and the thin liners are removed from the tissue-containing cast blocks.

An advantage of this embodiment of the invention is that the need for a spongy material to hold down the tissue during spinning is eliminated. Spongy material may be disadvantageous in certain circumstances because it tends to retain the various processing materials and may not become fully saturated with liquid embedding material.

The invention provides for automatically processing tissue samples from initial fixation to embedding. Importantly, the novel use of centrifugal force to drive processing liquids from tissue samples provides full assurance that previous processing liquids are removed before successive processing liquids or liquified embedding material is introduced. At the completion of a processing and embedding cycle, the tissue samples are still in the precise orientations selected by the technician and are in condition for slicing without further preparation.

While the invention has been described in terms of a preferred embodiment, modifications obvious to one with ordinary skill in the art may be made without departing from the scope of the invention.

Various features of the invention are set forth in the following claims.

What is claimed is:

1. Apparatus for processing and embedding tissue samples comprising rotor means having a rotational axis and a plurality of well means outward of its rotational axis for holding tissue samples, means to successively supply processing liquids and liquid embedding material to said well means, means to intermittently rotate said rotor means at a sufficient speed to slough liquid from said well means, and well cover means which retain said tissue samples in said well means while accessing processing liquids and embedding liquids to said well means, said well cover means comprising a peripheral frame defining a fluid passage opening and a porous mesh spanning said opening.

2. Apparatus according to claim 1 including means to heat said rotor means.

3. Apparatus in accordance with claim 1 wherein said well means are shallow trays pivotably mounted on said rotor and adapted to pivot from a horizontal position when said rotor is at rest to a vertical position when said rotor is rotated.

4. Apparatus according to claim 1 wherein said rotor has a central well means and channels means extending radially therefrom to said well means, whereby said well means is supplied with processing liquids and liquified embedding material from said central well means through said channel means.

5. Apparatus according to claim 4 wherein said channel means extend radially outward from said outward well means providing a liquid flow pathway for liquid spun from said well means.

6. Apparatus according to claim 1 wherein said means to successively supply processing and liquified embedding material to said well means comprises a plurality of reservoirs containing processing liquids and liquified embedding material and means to individually communicate said reservoirs to said well means.

7. Apparatus according to claim 6 including automatic programmable control means for successively communicating said reservoirs to said well means and intermittently actuating said rotor means to spin liquids therefrom, according to a processing cycle.

8. Apparatus according to claim 1 including a shroud surrounding said rotor for collecting processing liquids that overflow from said well means and which are spun from said well means.

9. Apparatus according to claim 8, said shroud having a lower sump opening.

10. Apparatus according to claim 8 having an open upper end and shroud cover means for closing off said open upper end.

11. Apparatus according to claim 8, said rotor having a central well means and channel means extending radially therefrom to said outward well means, said rotor cover having a central inlet conduit that leads externally, whereby liquid may be introduced to said central well means through said inlet conduit and flow through said radial channel means to said outward well means.

12. Apparatus according to claim 8 including sealing means between said cover and said shroud and means to communicate the interior of said shroud to vacuum for vacuum-embedding tissue samples within said well means.

13. Apparatus for processing and embedding tissue samples comprising rotor means having a rotational axis and a plurality of well means outward of its rotational axis for holding tissue samples, means to successively supply processing liquids and liquified embedding material to said well means, means to intermittently rotate said rotor means at a sufficient speed to slough liquid from said well means, and well cover means which retain said tissue samples in said well means while accessing processing liquids and embedding liquids to said well means, said well cover means comprising a peripheral frame defining a fluid passage opening and a porous mesh spanning said opening below an upper surface of said peripheral frame providing a region for embedding material above said mesh, whereby when liquified embedding material solidifies, said mesh is embedded therein and said cover is attached to said solidified embedding material.

14. Apparatus in accordance with claim 13 wherein said well cover means is detachable from said rotor and adapted to be inserted into a microtome chuck, whereby said solidified embedding material may be positioned for microtome slicing.

* * * * *